United States Patent [19]
Valentine et al.

[11] Patent Number: 5,985,624
[45] Date of Patent: Nov. 16, 1999

[54] PROCESS FOR THE FERMENTATIVE PREPARATION OF CLAVAM DERIVATIVES WHEREBY THE LEVELS OF AMMONIA AND UREA IN THE FERMENTATION MEDIUM ARE KEPT LOW

[75] Inventors: Brian Peter Valentine, Worthing; Paul Alan Jeffkins, Brighton; William Henry Holms; David Michael Mousdale, both of Glasgow, all of United Kingdom

[73] Assignee: SmithKline Beecham p.l.c., Middlesex, United Kingdom

[21] Appl. No.: 08/860,043

[22] PCT Filed: Dec. 7, 1995

[86] PCT No.: PCT/EP95/04888

§ 371 Date: Aug. 26, 1997

§ 102(e) Date: Aug. 26, 1997

[87] PCT Pub. No.: WO96/18743

PCT Pub. Date: Jun. 20, 1996

[30] Foreign Application Priority Data

Dec. 10, 1994 [GB] United Kingdom .................. 9424950

[51] Int. Cl.⁶ ..................... C12P 7/40; C07D 487/08; C12N 1/20
[52] U.S. Cl. ................... 435/119; 435/136; 435/886; 514/210; 540/349
[58] Field of Search ................... 435/119, 136, 435/886; 514/210; 540/349

[56] References Cited

U.S. PATENT DOCUMENTS 4,110,165  8/1978  Cole et al. .............................. 435/119
5,185,139  2/1993  Krishnamurthy et al. .............. 423/359

FOREIGN PATENT DOCUMENTS 1508977  4/1978  United Kingdom .

OTHER PUBLICATIONS

Romero et al. Appl. Microbiol. Biotechnol. vol. 20, pp. 318–325, 1984.
Zhang et al. Can. J. Microbiol. vol. 35, pp. 399–402, 1989.
Zhang et al. Biotechnol. Adv. vol. 9 (4), pp. 623–642, 1991.
Aharonowitz et al. Can. J. Microbiol. vol. 25, pp. 61–67, 1979.
Bascaran et al., "Regulationof Nitrogen Catabolic Enzymes in Streptomyces clavuligerus", *Journal of General Microbiology*, 135, 2465–2474 (1989).

*Primary Examiner*—Leon B. Lankford, Jr.
*Assistant Examiner*—Christopher R. Tate
*Attorney, Agent, or Firm*—Zoltan Kerekas; Stephen Venetianer; Charles M. Kinzig

[57] ABSTRACT

Improved methods for the preparation of clavams by fermentation of a clavam-producing organism in a suitable medium wherein the ammonium levels are kept low so as to avoid repression of enzymes, particularly urease, are disclosed.

10 Claims, No Drawings

PROCESS FOR THE FERMENTATIVE PREPARATION OF CLAVAM DERIVATIVES WHEREBY THE LEVELS OF AMMONIA AND UREA IN THE FERMENTATION MEDIUM ARE KEPT LOW

This appln is a 371 of PCT/EP95/0488 filed Dec. 7, 1995

This invention relates to a process for increasing the production of clavulanic acid and other clavams including those with a strong beta-lactamase inhibitory activity from organisms having the appropriate biosynthetic pathways.

Micro-organisms, in particular Streptomyces sp. produce a number of antibiotics including clavulanic acid and other clavams, cephalosporins and penicillins.

Clavulanic acid is an important beta-lactamase inhibitor which is a key ingredient of the antibiotic sold under the name AUGMENTIN (Trade Mark of SmithKline Beecham plc). The commercial method by which clavulanic acid is produced is via fermentation of *Streptomyces clavuligerus*. A suitable fermentation medium for producing clavulanic acid is described in UK Patent Specification No. 1,508,977.

Whilst clavulanic acid and other clavams can be prepared in acceptable amounts by existing methods there remains a need for improving the titre of clavulanic acid in the fermentation broth so that the product can be produced more economically. One way in which the problem can be addressed is to seek mutant strains of *Streptomyces clavuligerus* ATCC 27064 or other clavulanic acid-producing microorganisms which give rise to higher titre. To date relatively little has been published regarding process improvements by which a higher titre of clavulanic acid can be achieved by varying the reaction conditions in the fermentor.

It is customary to include ammonia as a source of nitrogen as manipulation of the nitrogen input to the fermentation is critical to clavulanic acid yield. However we have found that fermentation methods for producing clavulanic acid are particularly sensitive to the concentration of ammonia in the system.

According to the present invention there is provided a method for preparing clavams by fermentation of a clavam—producing organism in a suitable medium, characterised in that the amount of ammonia in the fermentation is kept at a low level during the fermentation in order to avoid repression of one or more key enzymes by ammonia.

By a low level we mean less than about 50 $\mu$g/ml. The level of ammonia should be maintained below 50 $\mu$g/ml for sufficient time, suitably between 1 and 10 hours, to allow derepression and biosynthesis of the key ammonia-repressible enzymes. Under customary fermentation conditions (with ammonia levels exceeding 100 $\mu$g/ml) it has been found that the ammonia acts to repress a number of enzymes involved in the metabolism of nitrogen including urease which catalyses the conversion of urea to ammonia and carbon dioxide ( See V. Bascaran et al. J. Gen Microbiol. 1989 vol 135 pp 2465 to 2474 ). However the latter studies were not linked to antibiotic titre and made no suggestion for any link with improvement in clavam or clavulanic acid production in particular.

A surprising finding in the work leading up to the present invention was that urea accumulates in clavulanic acid fermentation broths. Urea is produced from the clavulanic biosynthetic process but there may well be other sources of this urea.

It has been found in accordance with a further aspect of the present invention that if the urea which can build up during clavulanic acid production is caused to react with a urease enzyme titres of clavulanic acid are considerably improved, for example in the order of 10%.

Accordingly in a further aspect of the invention there is provided a method for preparing clavams by fermentation of a clavam-producing micro-organism in a suitable medium characterised in that urea produced during the fermentation process is caused to react with a urease enzyme.

The urease can be either intrinsic (endogenous) or extrinsic (exogenous), that is to say can be caused to be produced by the clavulanic acid producing micro-organism (intrinsic urease) or added to the system (extrinsic urease).

If it is desired to use extrinsic urease the enzyme may be obtained from any suitable source and added to the fermentation reaction. If the urease is intrinsic it can, in one aspect of the invention, be liberated by derepressing expression of urease by the clavulanic acid producing organism.

Such derepression may be caused, for example, by adjustment of the pH by any suitable base other than ammonia. In this method the concentration of ammonia in the fermentation is preferably lowered until derepression occurs. Such derepression may suitably be monitored by studying changes in the pH profile of the reaction medium (see examples below).

In the above method the pH control agent can be any suitable base other than ammonia, for example an alkali metal hydroxide such as sodium hydroxide. Once derepression has occurred and urease has been expressed it is advantageous to control pH in the usual way in order to ensure a sufficient nitrogen supply. Optionally however, a pH regulant other than ammonia may be used throughout the fermentation.

Ammonia is generally preferred as a feed in the typical fermentation as it has the dual purpose of pH regulation and introduction of nitrogen to the fermentation. It also acts as an ionic counterbalance to the clavulanate accumulating. Whilst the advantage gained by derepression of the ammonia-repressible enzymes can be achieved by the process of using an alternative pH regulant during part of the fermentation, it can also be achieved by using an alternative pH regulant and then introducing the required nitrogen to the fermentation in the batch or by feeding an ammonium salt.

In a further method of derepressing urease an adjustment may be made to the amount of complex nitrogen source batched or fed to the fermentation. Ammonia released by deamination of the complex nitrogen source will repress urease. Therefore an adjustment to the amounts included in the fermentation or their release characteristics will affect urease derepression.

A further method of increasing clavulanic acid titre is to add to the fermentation reaction any suitable compound which directly or indirectly affects the concentration of ammonia or urea in the fermentation.

One way in which this can be achieved is to add a compound such as a zeolite capable of adsorbing ammonia and so reducing its concentration. Suitable ammonia adsorbing reagents include those capable of precipitating ammonia as a complex salt, for example as ammonium magnesium phosphate.

A further way in which the concentration of urea may be decreased is to add a compound to the fermentation medium which directly or indirectly increases the expression of urease from the clavulanic acid producing organism.

Genetic manipulation or strain improvement methods may also be used to increase the levels of intrinsic urease produced by the clavulanic acid producing microorganism. For example strain improvement [e.g. by mutagenesis and subsequent selection on specific media such as those including methylammonium (Microbiological Reviews; 1989; 53, 85–108) can be used to prepare a mutant strain of clavulanic acid producing micro-organism which is constituitive for urease expression, i.e. urease is not subject to significant repression in the presence of ammonia. Similar results may be obtained by targeted genetic manipulation techniques, including manipulation of the urease gene so as to affect its regulation, for example causing concerted expression with an enzyme involved in the clavulanic acid biosynthetic pathway.

The above methods have the advantage that substantial increases in clavulanic acid titre can be achieved. The clavulanic acid may be separated and purified by standard techniques.

The following examples illustrate the invention. In the examples, unless otherwise indicated the methods and standard techniques used are as given in Sambrook et al (1989) Molecular Cloning: A Laboratory Manual, 2nd Edition.

EXAMPLE 1

Effect of Adjustment of the pH Regulant on Clavulanic Acid Titre

In a *Streptomyces clavuligerus* fermentation at 1000 litre scale (5% seed fermentation inoculum, soymeal protein between 20 and 60 g/l, dextrin between 1 to 3%, vegetable oil 1 to 5% plus a trace element cocktail with pH maintained at 6.8) the clavulanic acid output can be improved by 8% by adjustment of the pH regulant.

If 2.5N NaOH is used instead of ammonia to maintain pH at 6.8 at the start of the fermentation two peaks in the pH profile are observed. The first corresponds to deamination of soyprotein which releases ammonia and hence pH increases. The second is due to derepression of urease which also releases ammonia. After the second peak is observed (this can be confirmed by lack of detection of urea by colorimetric means) the pH regulant is switched back to ammonia to ensure a sufficient nitrogen supply to the reaction medium.

EXAMPLE 2

Preparation of Organisms Constituitive for Urease

Mutagenised strains of *S. clavuligerus* can be produced which constitutively express urease. Spores which have been subjected to a mutagen (such as UV radiation or exposure to nitrosoguanidine) are plated on agar containing methylammonium and urea. In the agar, urea is the sole carbon and nitrogen source. The methylammonium can not be metabolised but is recognised by the organism as ammonium and hence has a repressive effect on urease expression.

Mutant spores able to grow on this medium can be selected and shown to express urease in a constituitive manner in a fermentation and to give excellent clavulanic acid output.

What is claimed is:

1. A method for preparing clavams in a fermenter, which comprises:
   (a) fermenting a clavam-producing organism in a suitable medium; and
   (b) monitoring and controlling during fermentation ammonium levels in the fermenter to maintain to maintain ammonium at low levels that avoid reprision of urease.

2. The method according to claim 1 wherein the ammonium levels are less than 50 $\mu$g/ml.

3. The method according to claim 1 wherein the pH of the fermentation is adjusted by any suitable base other than ammonia.

4. The method according to claim 3 wherein the base is sodium hydroxide.

5. The method according to claim 1 wherein after derepression has occurred and urease has been expressed, pH is thereafter controlled by ammonia so as to ensure a sufficient nitrogen supply.

6. The method according to claim 1 wherein the ammonium is derived from a complex nitrogen source.

7. The method according to claim 1 wherein a compound is added to the fermentation which directly or indirectly affects the concentration of ammonia or urea in the fermentation or increases the expression of urease.

8. The method according to claim 7 wherein the compound is an ammonium adsorbing compound or precipitating compound.

9. The method according to claim 1 for preparing a clavam wherein the clavam is clavulanic acid.

10. The method according to claim 1 wherein the organism is *Streptomyces clavuligerus*.

\* \* \* \* \*

UNITED STATES PATENT AND TRADEMARK OFFICE
CERTIFICATE OF CORRECTION

PATENT NO. : 5,985,624
DATED : 16 November 1999
INVENTOR(S) : Valentine, *et al.*

It is certified that error appears in the above-identified patent and that said Letters Patent is hereby corrected as shown below:

Title page under "Other Publications" after "Attorney, Agent, or Firm", please change "Zoltan Kerekas" to read "Zoltan Kerekes".

In claim 1, line 15, after "ammonium levels in the fermenter", please correct "to maintain to maintain ammonium" to read "to maintain ammonium".

In claim 1, line 16, after "at low levels that avoid," please correct "reprision" to read "repression".

Signed and Sealed this

Fourth Day of July, 2000

*Attest:*

Q. TODD DICKINSON

*Attesting Officer*  *Director of Patents and Trademarks*